(12) United States Patent
Eastland

(10) Patent No.: US 8,101,142 B2
(45) Date of Patent: Jan. 24, 2012

(54) PROCESS AND PLANT

(75) Inventor: Philip Henry Donald Eastland, Teddington (GB)

(73) Assignee: Davy Process Technology Limited (GB)

( * ) Notice: Subject to any disclaimer, the term of this patent is extended or adjusted under 35 U.S.C. 154(b) by 0 days.

(21) Appl. No.: 10/158,752

(22) Filed: May 30, 2002

(65) Prior Publication Data
US 2002/0198267 A1 Dec. 26, 2002

(30) Foreign Application Priority Data

May 30, 2001 (GB) .................................. 0113078.0

(51) Int. Cl.
*B01J 8/04* (2006.01)
*C07C 27/00* (2006.01)

(52) U.S. Cl. ........ 422/630; 422/631; 422/637; 422/638; 422/200; 518/706

(58) Field of Classification Search .......... 422/187–193, 422/196–197, 198, 200, 211, 218, 630–632, 422/636–638, 201; 518/702, 704–707, 712
See application file for complete search history.

(56) References Cited

U.S. PATENT DOCUMENTS

| | | | | |
|---|---|---|---|---|
| 1,036,473 A * | 8/1912 | Eschellmann et al. | ........ | 423/537 |
| 1,868,096 A | 7/1932 | Dreyfus | | |
| 1,945,353 A * | 1/1934 | Jaeger | ............................ | 422/190 |
| 2,149,515 A * | 3/1939 | Fischer | ......................... | 518/706 |
| 2,279,153 A * | 4/1942 | Wilcox | ......................... | 518/707 |
| 3,950,369 A | 4/1976 | Gent | ............................ | 260/449.5 |
| 4,235,799 A | 11/1980 | Wentworth et al. | ........ | 260/449.5 |
| 4,298,694 A * | 11/1981 | Skov | ............................ | 518/704 |
| 4,321,234 A * | 3/1982 | Ohsaki et al. | ................. | 422/200 |
| 4,546,111 A * | 10/1985 | Banquy | ......................... | 518/703 |
| 4,568,530 A | 2/1986 | Mandelik et al. | .............. | 423/359 |
| 4,594,227 A | 6/1986 | Ohsaki et al. | ................. | 422/148 |

(Continued)

FOREIGN PATENT DOCUMENTS
DE 3540457 A1 * 5/1987
(Continued)

OTHER PUBLICATIONS

"MRF Reactor Commercially Proven Performance in a Methanol Plant," Crocco & Associates, Inc., p. VIII-1-VIII-10; Dec. 1990.

*Primary Examiner* — Jennifer A Leung
(74) *Attorney, Agent, or Firm* — Davidson, Davidson & Kappel (57) ABSTRACT

A reactor system, plant and a process for the production of methanol from synthesis gas is described in which the reactor system comprises:
(a) a first reactor adapted to be maintained under methanol synthesis conditions having inlet means for supply of synthesis gas and outlet means for recovery of a first methanol-containing stream, said first reactor being charged with a first volume of a methanol synthesis catalyst through which the synthesis gas flows and on which in use, partial conversion of the synthesis gas to a product gas mixture comprising methanol and un-reacted synthesis gas will occur adiabatically; and
(b) a second reactor adapted to be maintained under methanol synthesis conditions having inlet means for supply of the gaseous first methanol-containing stream, outlet means for recovery of a second methanol-containing stream and cooling means, said second reactor being charged with a second volume of a methanol synthesis catalyst through which the gaseous first methanol-containing stream flows and on which, in use, further conversion of the synthesis gas to a product gas mixture comprising methanol will occur.

17 Claims, 5 Drawing Sheets

U.S. PATENT DOCUMENTS

| | | | | |
|---|---|---|---|---|
| 4,714,592 A | * | 12/1987 | Zanma et al. | 422/192 |
| 4,766,154 A | | 8/1988 | Bonnell et al. | 518/700 |
| 4,778,662 A | * | 10/1988 | Pinto | 422/148 |
| 4,867,959 A | | 9/1989 | Grotz | 423/360 |
| 5,216,034 A | | 6/1993 | Sie | 518/706 |
| 5,266,281 A | * | 11/1993 | Kao et al. | 422/197 |
| 5,405,586 A | | 4/1995 | Koves | 422/218 |
| 5,427,760 A | | 6/1995 | Grotz | 423/360 |
| 5,472,986 A | * | 12/1995 | van Dijk | 518/705 |
| 5,512,255 A | | 4/1996 | Coffman | 422/201 |
| 5,610,202 A | | 3/1997 | Marchionna et al. | 518/700 |
| 5,631,302 A | | 5/1997 | König et al. | 518/706 |
| 5,723,084 A | | 3/1998 | Shin | 264/205 |
| 5,827,901 A | | 10/1998 | König et al. | 518/706 |

FOREIGN PATENT DOCUMENTS

| | | | |
|---|---|---|---|
| EP | 314550 A1 | * | 5/1989 |
| ES | 8608919 | | 10/1994 |
| GB | 1356151 A | * | 1/1973 |
| WO | WO 99/59945 | * | 11/1999 |

* cited by examiner

PRIOR ART

PROCESS AND PLANT

BACKGROUND OF THE INVENTION

The present invention relates to a process, reactor system and plant for the production of methanol. In particular, it relates to a process, reactor system and plant for producing methanol from hydrogen and carbon oxides.

Methanol is synthesised in large volumes annually by the conversion of a carbonaceous feedstock, such as natural gas, into a mixture of carbon oxides and hydrogen. Such a mixture of gases in often referred to as synthesis gas.

The conversion of a hydrocarbon-containing feedstock, such as natural gas, into synthesis gas can be achieved by steam reforming, by partial oxidation, or by a combination of these processes.

In steam reforming a mixture of desulphurised hydrocarbon feedstock, such as natural gas, and steam is passed at high temperature, typically at a temperature of from about 600° C. to about 1000° C., and elevated pressure, typically from about 10 bar up to about 50 bar, over a suitable reforming catalyst, such as a supported nickel catalyst. One commercially recommended catalyst which is suitable for this purpose uses a mixture of calcium and aluminium oxides as support for the nickel. The principal reaction is:

$$CH_4 + H_2O \rightleftharpoons CO + H_2.$$

The reaction products themselves are further subject to the reversible "water gas shift" reaction in which carbon dioxide and hydrogen are produced from carbon monoxide and steam:

$$CO + H_2O \rightleftharpoons C_2 + H_2.$$

Another method for producing synthesis gas involves the use, wholly or in part, depending upon the carbon to hydrogen ratio in the hydrocarbonaceous feedstock, of direct catalytic or non-catalytic partial oxidation or secondary/autothermal reforming with oxygen. In the case of methane this occurs according to the following equation:

$$CH_4 + \tfrac{1}{2}O_2 \rightleftharpoons CO + H_2.$$

A combination of steam reforming and partial oxidation or secondary/autothermal reforming can also be used.

Conversion of the carbon oxides and hydrogen to methanol occurs according to the following reactions:

$$CO + 2H_2 \rightleftharpoons CH_3OH$$

$$CO_2 + 3H_2 \rightleftharpoons CH_3OH + H_2O.$$

These reactions are conventionally carried out by contacting the synthesis gas with a suitable methanol synthesis catalyst under an elevated synthesis gas pressure, typically in the range of from about 50 bar up to about 100 bar, usually about 80 bar, and at an elevated methanol synthesis temperature, typically from about 210° C. to about 270° C. or higher, e.g. up to about 300° C.

Suitable methanol synthesis catalysts include copper containing catalysts with a catalyst comprising a reduced zinc oxide/copper oxide mixture being particularly suitable.

As with many reactions it is desirable to achieve the maximum rate of reaction per weight of catalyst or per volume of the reactor.

A conventional methanol synthesis plant can be considered to comprise four distinct parts, namely:
1. a reforming plant, which produces a mixture of carbon oxides and hydrogen from a hydrocarbon feedstock;
2. a compression stage which lifts the carbon oxides and hydrogen mixture to a higher pressure suitable for downstream methanol synthesis;
3. a methanol synthesis section, in which crude methanol is produced from the carbon oxides and hydrogen; and
4. a distillation section, in which the final refined methanol product is produced from the crude methanol.

A number of different types of reformer for use in part 1 of the methanol synthesis plant i.e. the reforming plant, are known in the art. One such type is known as a "compact reformer" and is described in WO-A-94/29013, which is incorporated herein by reference and which discloses a compact endothermic reaction apparatus in which a plurality of metallic reaction tubes are close-packed inside a reformer vessel. Fuel is burned inside the vessel, which comprises air and fuel distribution means to avoid excessive localised heating of the reaction tubes. In a compact reformer of this type heat is transferred from the flow gas vent and from the reformed gas vent of the reformer to incoming feedstock, fuel and combustion air. Other types of reformer are not as efficient as the compact reformer in transferring heat internally in this way. However, many other reformer designs are known and some are described in EP-A-0033128, U.S. Pat. Nos. 3,531,263, 3,215,502, 3,909,299, 4,098,588, 4,692,306, 4,861,348, 4,849,187, 49,090,808, 4,423,022, 5,106,590 and 5,264,008, 5,264,008 and WO 98/28071 which are incorporated herein by reference.

In a conventional plant, synthesis gas is compressed in passage from the reforming plant to the methanol synthesis zone. This compression stage is generally present in order to provide the required pressure of from 50 bar to 100 bar in the methanol synthesis zone. The compressed gas is then passed to the methanol synthesis section.

In U.S. Pat. No. 4,594,227 apparatus for carrying out a catalytic chemical reaction is described which comprises a vertical, annular, intercylinder space which is divided by radially extending vertical partition walls into a plurality of chambers some of which include heat-exchanging tubes. Segments containing no heat-exchanging tubes may be packed with catalyst and utilised adiabatically to preheat the reaction gases. In use, the reaction gases will pass outwardly through this first segment, where any reaction will cause heating, they then are transmitted through the annular space surrounding the intercylinder space before travelling inwardly through the segment containing catalyst and cooling tubes where further reaction will occur.

Whilst this arrangement does offer certain advantages, it also suffers from various drawbacks. A principle disadvantage arises from the multi-segmental radial flow. This flow pattern causes the gas velocity to vary as the flow traverses from the centre of the reactor to the outside and back, due to the changing cross-sectional area of the segments. This changing velocities of the segments causes the heat transfer coefficient between the reacting gases and the cooling medium in the tubes to vary. In particular the heat transfer will increase as the gas velocity increases and will decrease as the gas velocity is reduced.

Thus the multi-segmental arrangement of the radial flow apparatus in U.S. Pat. No. 4,594,227 does not allow the gas velocity pattern and resultant heat transfer pattern to be optimised.

Various methanol production processes are known in the art, and reference may be made, for example, to U.S. Pat. Nos. 5,610,202, 4,968,722, 5,472,986, 4,181,675, 5,063,250, 4,529,738, 4,595,701, 5,063,250, 5,523,326, 3,186,145, 344, 002, 3,598,527, 3,940,428, 3,950,369, WO-A-98/28248 and U.S. Pat. No. 4,051,300 which are incorporated herein by reference.

Various suggestions have been made for modifications to the plant design with a view to improving the economics of the production process.

Several suggestions for improving the efficiency of the reaction have been made which incorporate the use of multiple reaction stages. For example, in U.S. Pat. No. 5,631,302 it is suggested that the methanol synthesis section should include two separate synthesis reactors. In this arrangement, the synthesis gas is passed to the first synthesis reactor, which is a shaft reactor containing a fixed bed of a copper-containing catalyst. The reaction in this shaft reactor is carried out adiabatically and in the absence of any recycling of synthesis gas. The product stream from this first reactor, which contains methanol vapour, is cooled to condense the methanol which is separated from the unreacted gaseous components of the first product stream. These unreacted gaseous components are then compressed, heated and fed to the second reactor where they react to form methanol. The second reactor is preferably a tubular reactor in which the copper catalyst is indirectly cooled by water which is boiling under high pressure. The product stream from the second reactor is cooled and the methanol is removed by separation. Any unreacted gaseous components are compressed and heated before being returned to the second reactor.

Thus in U.S. Pat. No. 5,631,302 the first reactor is located outside the main reactor loop and simply serves to modify the composition of the feed gas before it enters the main reaction loop. The arrangement of U.S. Pat. No. 5,631,302 is said to be useful where the synthesis gas feed has a $CO_2$:CO ratio which exceeds 2:1.

An alternative arrangement is suggested in U.S. Pat. No. 5,827,901. In this arrangement two synthesis reactors are connected in series such that the product stream from the first reactor is passed directly to the inlet of the second reactor. The first reactor is a water cooled reactor in which the catalyst is located in tubes through which the gaseous reactants flow. The second reactor may be selected from a variety of designs. Whichever design is used, cooling in the second reactor is provided by counter-current heat exchange with the feed synthesis gas before it is fed to the first reactor.

This arrangement allows for cooler exit temperatures from the second reactor to be achieved than are conventionally achievable. However, whilst the lower temperature may allow the reaction equilibrium to move towards completion, it may also reduce the rate of reaction, and therefore may require more catalyst per unit of product.

Other examples include U.S. Pat. No. 5,427,760 in which two reaction stages are used in an attempt to achieve a higher overall conversion to the desired ammonia than can be achieved in a single stage and U.S. Pat. No. 4,867,959 in which two or more reaction stages are described, with cooling between each stage, to increase conversion. As discussed by Kobayashi and Green in a paper presented to the 1990 World Methanol Conference, this approach can be extended to include a large number of stages. This paper also illustrates the optimum rate line for methanol synthesis.

Whilst an optimum rate line is known, a near-optimum reaction profile is not practical in commercial arrangements. This is because such a profile would generally require the reaction to start at high temperature and gradually fall as the reaction proceeds. Some suggestions have been made to produce a system which approaches the optimum rate line, such as those in the Kobayashi and Green paper however, a commercially satisfactory arrangement has not been realised.

Thus it will be understood that whilst the systems of the prior art go some way to addressing the problems associated with reducing the operating and/or investment costs of producing methanol, various disadvantages and drawbacks remain and there is still a requirement for alternative arrangements which will address at least some of these problems.

SUMMARY OF THE INVENTION

One alternative arrangement which goes at least some way to addressing these problems is an arrangement in which the catalyst for the production of methanol in the methanol synthesis section of the plant is divided into two volumes of independent geometry. An arrangement of this type will allow the highest temperature to which the catalyst is subjected to be reduced whilst also reducing the overall reactor pressure drop.

Thus, according to a first aspect of the present invention there is provided a reactor system for use in the production of methanol from synthesis gas comprising:

(a) a first reactor adapted to be maintained under methanol synthesis conditions having inlet means for supply of synthesis gas and outlet means for recovery of a first methanol-containing stream, said first reactor being charged with a first volume of a methanol synthesis catalyst through which the synthesis gas flows and on which in use, partial conversion of the synthesis gas to a product gas mixture comprising methanol and unreacted synthesis gas will occur adiabatically; and (b) a second reactor adapted to be maintained under methanol synthesis conditions having inlet means for supply of the gaseous first methanol-containing stream, outlet means for recovery of a second methanol-containing stream and cooling means, said second reactor being charged with a second volume of a methanol synthesis catalyst through which the gaseous first methanol-containing stream flows outwardly from the inlet means and on which, in use, further conversion of the synthesis gas to a product gas mixture comprising methanol will occur. In one preferred arrangement the cooling means is arranged such that heat transfer decreases as the gas flows from the inlet to the outlet.

Thus the present invention provides an arrangement in which an adiabatic bed is combined with a downstream cooled catalyst bed. This arrangement allows a commercially acceptable process to be provided which, in the most preferred arrangement has a reaction profile which will approximately follow the optimum rate line.

In a preferred arrangement, the first and second reactors are separate reactors and the outlet means of the first reactor is connected to the inlet means of the second reactor by conventional means.

However, the first and second reactors may be zones located within a single reactor. In this latter arrangement it is important that the catalyst of the first and second reactors do not have a common face and the reactor system will therefore preferably include means for separating the two catalyst volumes and for transferring the gaseous first methanol-containing stream from the outlet means of the first reactor to the inlet means of the second reactor. It will be understood that in this arrangement the "outlet means" and "inlet means" may be areas of the reactor rather than specific items of construction. The or each reactor is preferably a pressure vessel.

The first volume of the methanol synthesis catalyst is preferably arranged as a horizontal volume and the apparatus is preferably arranged such that the synthesis gas preferably flows through the catalyst volume in a vertical direction. In a particularly preferred arrangement, the depth of the first volume of catalyst is preferably less than its horizontal dimensions. Thus, where the first volume of catalyst is cylindrical, the depth of the cylinder is less than the diameter of the cross-section of the cylinder or where it is a prism, the depth will be less than the cross-sectional dimensions.

One benefit associated with reducing the depth of the bed is that the pressure drop of the gases as they pass through the bed is reduced. This has the effect of reducing the overall cost of the plant. A further advantage of the arrangement of the present invention is that the increased cross-sectional area of the catalyst in the first volume presented to the synthesis gas relative to the depth of the first volume of catalyst through which the gas has to flow when compared to prior art catalyst volumes in vertical vessels facilitates the heat transfer by conduction and/or radiation from the relatively hotter catalyst at the bottom of the bed to the relatively cooler catalyst located towards the upper surface of the bed. The resultant increase in the average temperature of the catalyst bed serves to increase the rate of reaction.

Whilst the horizontal arrangement of the catalyst volume is preferred, any suitable arrangement may be utilised provided that it is of a low pressure drop design. In one alternative arrangement the first volume of catalyst in the first reactor allows for radial flow.

The first volume of catalyst will be retained in position within the reactor by any suitable means and is preferably located on a support means, such as a grid, which allows the gaseous reactants to pass through the catalyst volume with minimal reduction in gas pressure. The first catalyst volume is preferably a fixed bed arrangement.

The first reactor may additionally include an inlet gas distributor to assist in achieving good distribution of the synthesis gas throughout an upper area of the reactor before the gas comes into contact with the catalyst volume.

Any suitable arrangement for the second reactor may be used. Further any suitable arrangement for the second volume of catalyst in the second reactor may be used. In a preferred arrangement, the reactor is designed for a minimum pressure drop. In a most preferred arrangement, the second volume of catalyst in addition to providing minimum pressure drop is also arranged to allow good heat transfer from the catalyst to a cooling means. The presence of the cooling means is particularly preferred as it provides that the exit temperature of the gas is reduced towards the equilibrium value and is prevented from rising significantly which would result in faster rates of catalyst deactivation.

In a particularly preferred arrangement, the product stream from the first reactor flows radially from a central inlet to an outlet collector located at a reactor zone wall through the second catalyst volume.

The catalyst may be cooled by any suitable means. In one preferred arrangement, cooling is provided by boiling water cooling in tubes which pass through the catalyst bed in a conventional manner. This method of cooling allows steam to be produced which may then be used to drive the compressor which may be present to increases the pressure of the feed or recycle synthesis gas prior to its addition to the first reactor zone.

Producing the steam for use in driving the compressor in this manner has various benefits. In particular, the overall efficiency of the plant may be improved which will reduce the overall costs.

The catalyst in the first and second volumes may be the same or different. The catalyst for use in the methanol synthesis in each reactor is preferably selected from, but is not limited to, copper-containing catalysts, for example reduced CuO—ZnO catalysts. Preferred catalysts include those sold under the designation 51/8 by ICI Katalco. Other suitable catalysts are described in U.S. Pat. No. 6,054,497 which is incorporated herein by reference.

According to a second aspect of the present invention there is provided a plant for the production of methanol from a synthesis gas mixture comprising carbon oxides, hydrogen and methane comprising:
(a) a methanol synthesis zone including the reactor system according to the above-mentioned first aspect of the present invention; and
(b) a methanol recovery zone, adapted to be maintained under methanol recovery conditions, for recovery of a crude methanol product stream from the product gas mixture, and for recovery of a vaporous stream comprising unreacted material of the synthesis gas.

In a preferred arrangement the plant additionally includes:
(c) means for recycling at least a portion of the unreacted material of the synthesis gas from the methanol recovery system to the methanol synthesis zone.

The synthesis gas mixture is preferably produced from a hydrocarbon feedstock material in plant comprising a steam reforming zone, adapted to be maintained under steam reforming conditions and charged with a catalyst effective for catalysis of at least one steam reforming reaction, for steam reforming of a vaporous mixture of the hydrocarbon feedstock in the steam to form a synthesis gas mixture comprising carbon oxides, hydrogen and methane. Suitable steam reformers include those detailed above which are incorporated herein by reference.

The plant of the present invention may include a plurality of reactor systems according to the above first aspect of the present invention. These may be located in parallel such that the overall plant production of methanol may be increased or in an alternative arrangement, they may be located in series such that the second methanol-containing stream is passed either directly or indirectly to a first reactor zone of a second reactor system. One benefit of this arrangement is that the recovery of reactants is improved.

According to a third aspect of the present invention there is provided a process for producing methanol from a synthesis gas comprising:
(a) supplying the synthesis gas mixture to the methanol synthesis reactor system of the above-mentioned first aspect of the present invention maintained under methanol synthesis conditions;
(b) recovering from the methanol synthesis reactor system a product gas mixture comprising methanol and any unreacted material of the synthesis gas mixture;
(c) supplying material of the product gas mixture to a methanol recovery zone maintained under methanol recovery conditions; and
(d) recovering from the methanol recovery zone a crude methanol product stream and a vaporous stream comprising unreacted material of the synthesis gas mixture.

In a preferred arrangement, the process additionally includes the step of recycling the unreacted material of the synthesis gas mixture to the methanol synthesis reactor.

The synthesis gas is preferably formed from a hydrocarbon feedstock in a process comprising contacting a vaporous mixture comprising the feedstock and steam in the steam reforming zone with a catalyst effective for catalysis of at least one reforming reaction and recovering from the reforming zone a synthesis gas mixture comprising carbon oxide, hydrogen and methane.

The synthesis gas is preferably compressed before being supplied to the methanol synthesis reactor system. The pressure of the gaseous reactants entering the first reactor zone will preferably be in the region of 20 bar to 200 bar. The first volume of catalyst in the first reactor is preferably arranged such that the gas pressure drop that occurs is less than 0.5 bar. The compression may occur by any suitable means. Typically the motive force of gas compression is provided by high pressure steam generated within the plant by a steam turbine. However, as has been discussed, the steam may be wholly or in part provided by the cooling system in the second reactor.

The temperature of the gaseous reactants entering the first reactor will preferably be in the region of about 180° C. to about 220° C. The reactants exiting the first reactor and entering the second reactor will be substantially the same temperature. The temperature of these streams is most preferably just below peak reaction temperature and will therefore most preferably be in the region of about 230° C. to about 350° C.

The space velocity of the synthesis gas mixture entering the first volume of catalyst is preferably in the region of 5 to 20% of the total space velocity, dependent on the syntheses gas composition.

The apparatus, plant and process of the present invention have significant advantages over conventional apparatus, plant and processes for the production of methanol.

Most significantly the invention allows the first volume of catalyst to be designed to give a low pressure drop, while the second volume of catalyst is designed to meet the additional requirement to control reaction temperature. By separating the two volumes flexibility is attained which leads to enhanced performance of the reactor in terms of reactor pressure drop, steam production pressure and reactor conversion.

One further benefit of the present invention is that the arrangement in the first reactor zone is simple to manufacture which substantially reduces the cost of construction.

Whilst generally there is no economic benefit in dividing volumes of material in process plants, since this inevitably leads to an increase in aspects of reactor construction cost per unit volume, in the present invention substantial benefits are obtained.

For example, by reducing the reaction system pressure drop, the requirement to compress the recycle gas stream is reduced and hence the cost of recycle gas compression is reduced. A slight increase in conversion of synthesis gas to methanol may also be noted. However, more importantly, the improved efficiency of the present invention may mean that the total catalyst volume required for a given methanol production rate is reduced.

The system has the further benefit in that the maximum temperature achieved in the reaction zones is reduced which will reduce the rate at which catalyst deactivation occurs.

BRIEF DESCRIPTION OF THE DRAWINGS

The present invention will now be described, by way of example, with reference to the accompanying drawings in which.

DETAILED DESCRIPTION OF THE INVENTION

It will be understood by those skilled in the art that the drawings are diagrammatic and that further items of equipment such as feedstock drums, pumps, vacuum pumps, compressors, gas recycling compressors, temperature sensors, pressure sensors, pressure relief valves, control valves, flow controllers, level controllers, holding tanks, storage tanks and the like may be required in a commercial plant. Provision of such ancillary equipment forms no part of the present invention and is in accordance with conventional chemical engineering practice.

Figure 1:
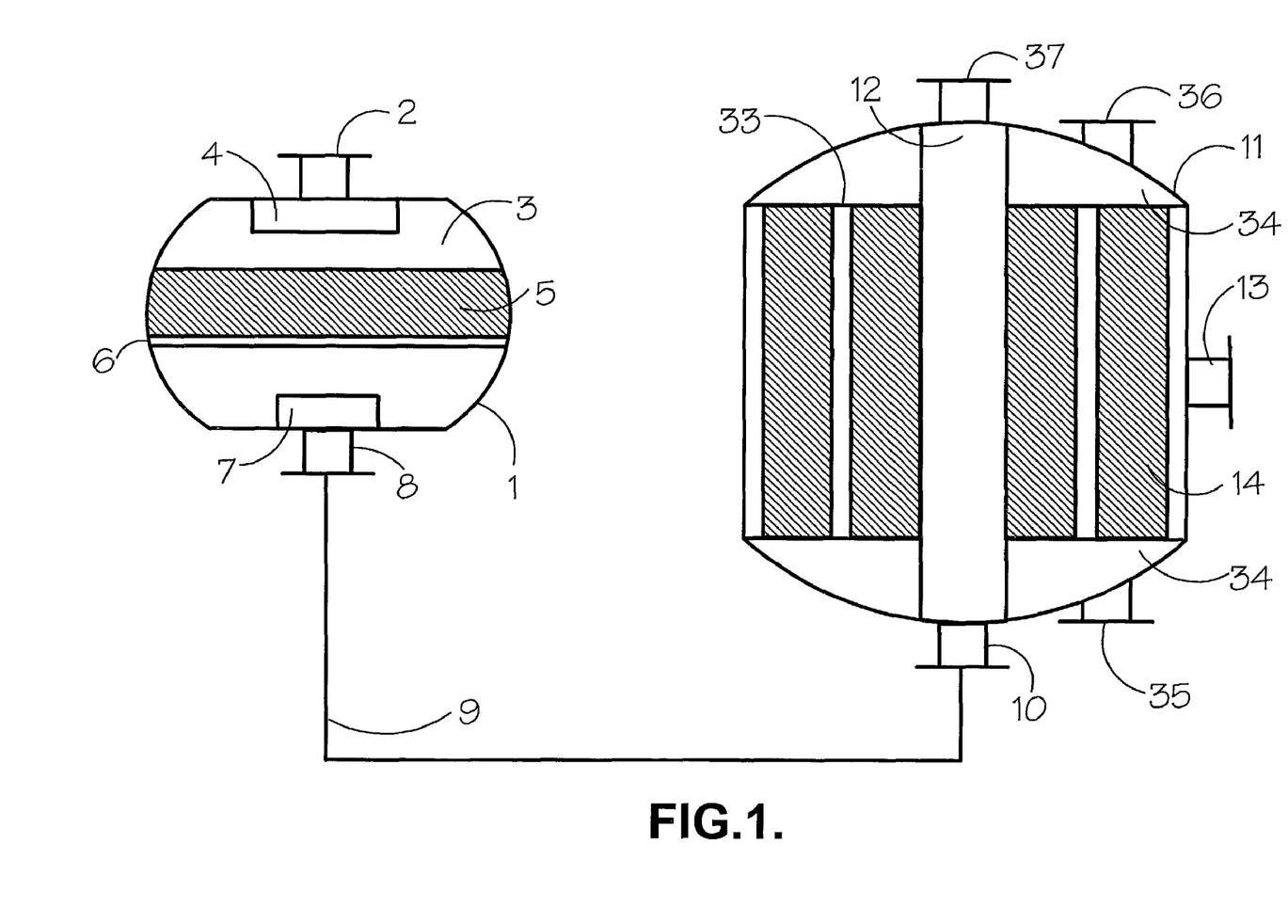
FIG. 1 is a representation of a reactor system in accordance with the present invention.

Referring to FIG. 1, the methanol reaction system of the present invention comprises a first reactor vessel 1 having a gas inlet 2 and through which in use synthesis gas at a temperature of 180° C. to 220° C. and a pressure of 20 bar to 200 bar enters. The gas is preferably evenly distributed within the upper area 3 of the vessel 1 by means of an inlet gas distributor 4.

The synthesis gas then passes through a first volume of catalyst comprising a bed of a suitable methanol synthesis catalyst 5 supported on a grid 6. The catalyst is preferably a copper-containing catalyst such as CuO—ZnO. The bed of catalyst 5 has a high cross-section to depth ratio when compared with conventional systems. The depth of the bed is preferably between about 0.4 to about 1.2 meters. This low depth to the catalyst bed reduces the pressure drop of the gaseous mixture as it passes through the bed.

Some of the synthesis gas will undergo conversion adiabatically to methanol as it is passed through the catalyst bed 5 such that the gases collected by the gas collector 7 include un-reacted synthesis gas and methanol. This then leaves reactor 1 via outlet 8 and the gaseous stream is passed in line 9 to the inlet 10 to the second reactor zone 11.

This second reactor may be of any suitable design but preferably has a central gas distributor 12 and is constructed to allow for radial gas flow from the central gas distributor 12 to the outlet collector 13 at the vessel wall of reactor 11. Thus gas flow is predominantly radial such that the gaseous mixture will pass through the catalyst bed 14.

The bed 14 is cooled by water boiling in a plurality of tubes 33 which pass through the catalyst bed between tube sheets 34 located above and below the catalyst bed. Pressurised cooling water is introduced via inlet nozzle 35 and steam and water exits via the exit nozzle 36. The reactor also includes a utility nozzle 37.

Figure 2:
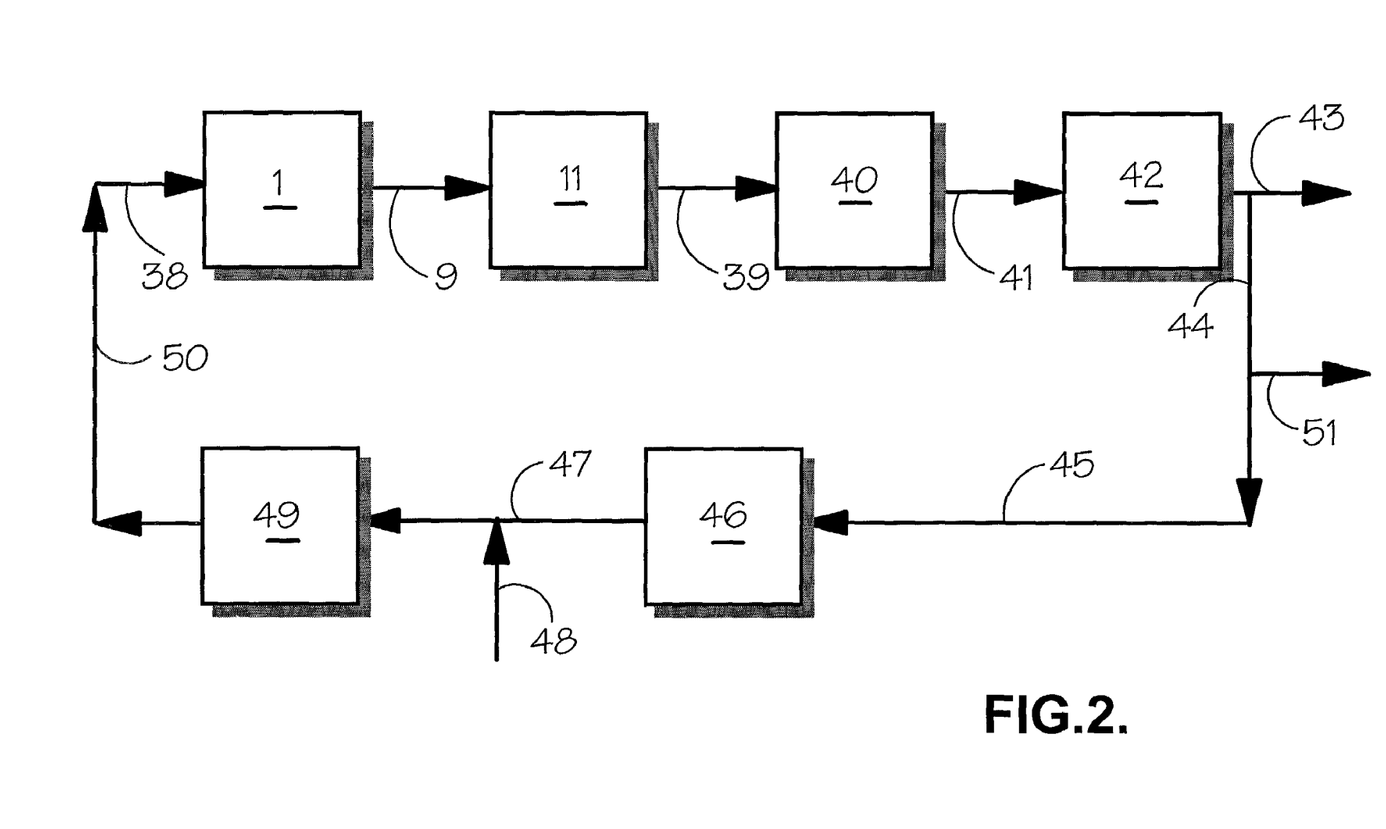
FIG. 2 is a schematic diagram of a process in accordance with the present invention.

FIG. 2 illustrates the flow sheet of the process of the present invention in which synthesis gas, which may have been formed in a steam reforming plant (not shown) is fed at a pressure of from 20 bar to 200 bar at a temperature of from about 180° C. to about 220° C. to the first reactor volume 1 in stream 38 where reaction occurs adiabatically.

The first product stream which will be at a pressure from about 20 bar to about 200 bar and a temperature of from about 200° C. to about 250° C. and which includes un-reacted synthesis gas and methanol is passed to the second reactor volume 11 where further reaction occurs. The product stream 39 collected from the second reactor 11 is passed to the cooling heat exchanger train 40 where the methanol is condensed. Stream 41 is therefore of mixed phase including un-reacted synthesis gas and condensed methanol. These are separated in separator 42 and a crude methanol product stream is retrieved in line 43 for further purification by conventional means such as distillation.

The gas stream 44 from the separator will generally be divided into a recycle stream 45 and a purge gas stream 51. The purge gas stream will remove inert materials and optionally excess hydrogen.

Gas stream 45 is then compressed in gas compressor 46 to a sufficient pressure to allow recycling to the first reactor zone 1. The resultant stream 47 may be combined with fresh synthesis gas via line 48. In one alternative arrangement, the fresh synthesis gas may be added into line 45, i.e. before the recycle stream is passed through the compressor.

The steam produced by the water cooling may be used to drive a compressor by conventional means, and the reactor system may include an apparatus to enable this.

The resultant stream will then pass through heat exchangers 49 before being passed in stream 50 to the first reactor zone 1.

In one arrangement the heat exchangers 40 and 49 may be combined such that the hot product stream 39 is cooled in counter-current heat exchange with the recycle stream 47 which is consequently warmed.

Figure 3:
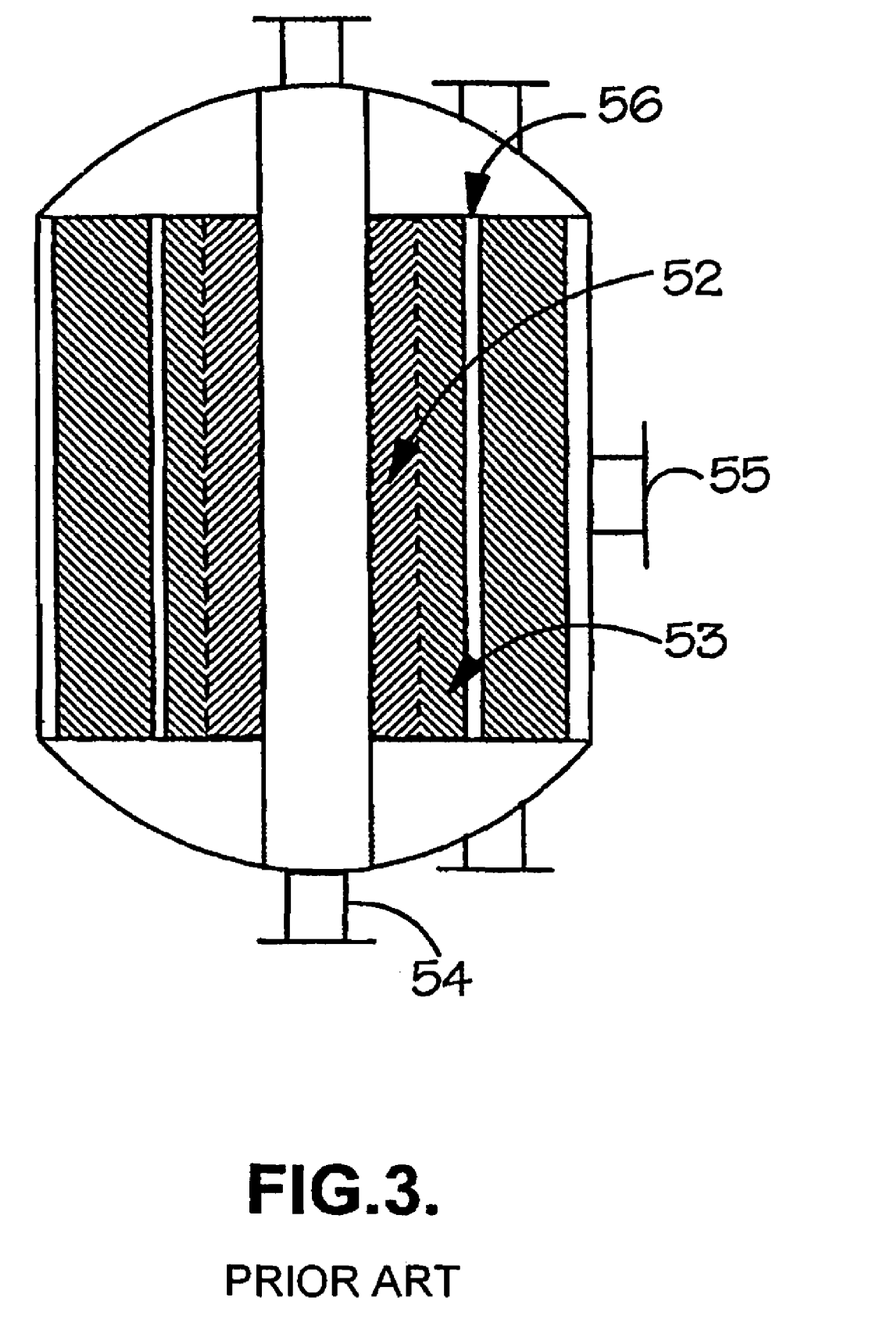
FIG. 3 is a representation of a reactor system according to the comparative example.

FIG. 3 illustrate an reactor of generally conventional design which will produce the same quantity of methanol from the same gas feed as that illustrated in FIG. 1. In this arrangement the conventional design has been slightly modified to more closely be comparable to the arrangement of FIG. 1 and thus on an inner part of the catalyst volume 52 has no cooling tubes passing through and therefore an essentially adiabatic bed is achieved through which the synthesis gas flows after entry through inlet 54.

As the gas flow is radial towards outlet 55, after passing through the inner volume, the gas passes through an other part 53 of the catalyst volume through which cooling tubes 56 pass. Thus the second part of the volume functionally corresponds with the second reactor of FIG. 1. However, in order to achieve the same production rate while maintaining the same vessel diameter, the height of the vessel has to be increased over that required in the arrangement of FIG. 1. This is partly due to the inclusion of the adiabatic volume of catalyst. However, it is also due to reduced gas velocities caused by the increased height over the increased mean diameter of the cooled catalyst volume which causes a lower heat transfer coefficient. Thus to remove the same amount of heat without increasing the peak catalyst temperature, a larger surface area and hence a large volume of cooling tubes has to be provided. The lower gas velocities also result in poorer heat transfer and thus poorer temperature control within the cooled bed.

Further an increased volume of catalyst is required since the exit temperature of the gas from the catalyst bed is reduced which reduces the rate of reaction per unit volume of catalyst. Thus, this arrangement would be wholly uneconomical.

Example 1 and Comparative Example 1

Reactive systems in accordance with those illustrated in FIG. 1 and FIG. 3 are fed with a feed gas having the following composition:

| Component | Volume % |
|---|---|
| Steam | 0.4 |
| Hydrogen | 72.5 |
| Carbon Monoxide | 15.4 |
| Carbon Dioxide | 7.3 |
| Methane | 3.3 |
| Nitrogen | 1.1 |
| Total | 100.0 |

The results obtained are as follows:

| | Example 1 | Comparative Example 1 |
|---|---|---|
| Catalyst Volume, relative | 1.0 | 1.1 |
| Methanol Production Per Unit Volume (relative) | 1.0 | 0.9 |
| Generated Steam pressure bar | 25.5 | 25.5 |
| Reactor Pressure Drop bar | 1.4 | 1.15 |
| Heat Transfer surface, relative | 1.0 | 1.09 |
| Inlet gas temperature ° C. | 221 | 218 |

Figure 4:
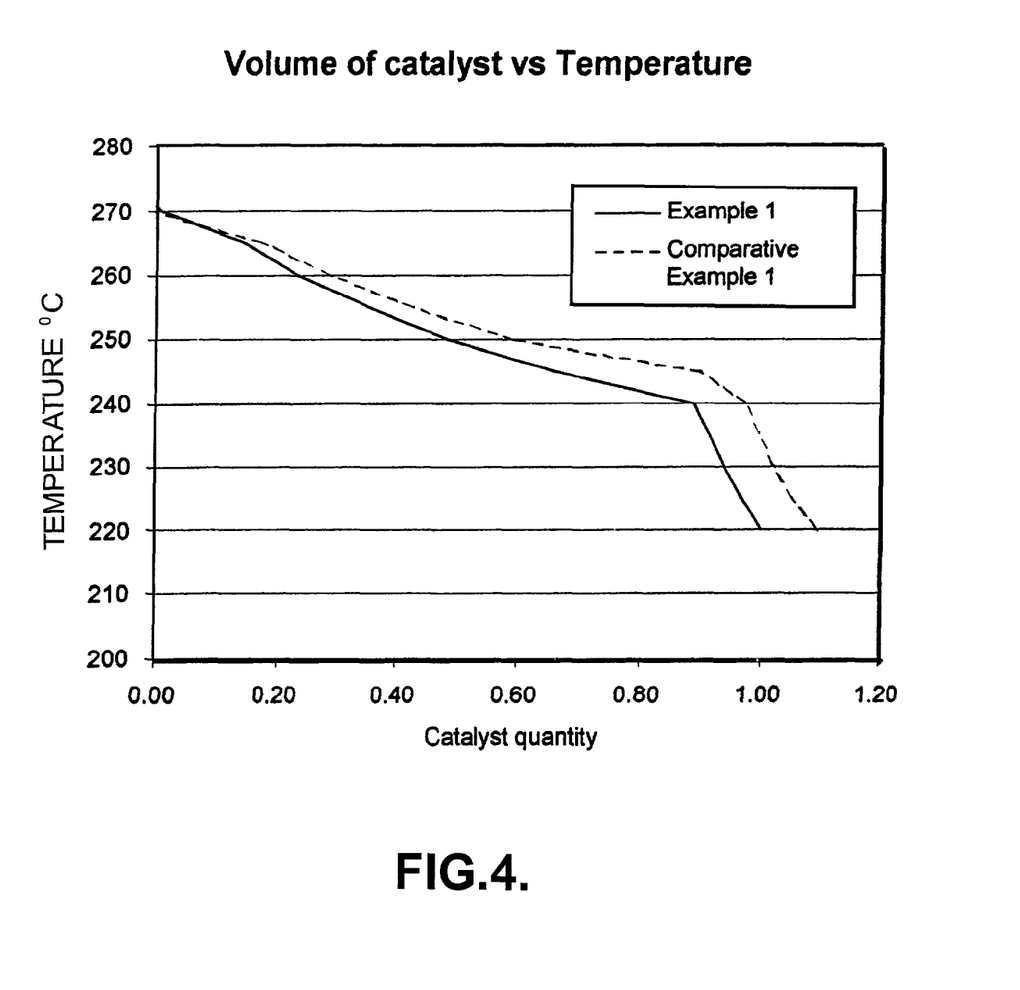
FIG. 4 is a graph comparing results obtained in reactions in the system of FIGS. 1 and 3.
Figure 5:
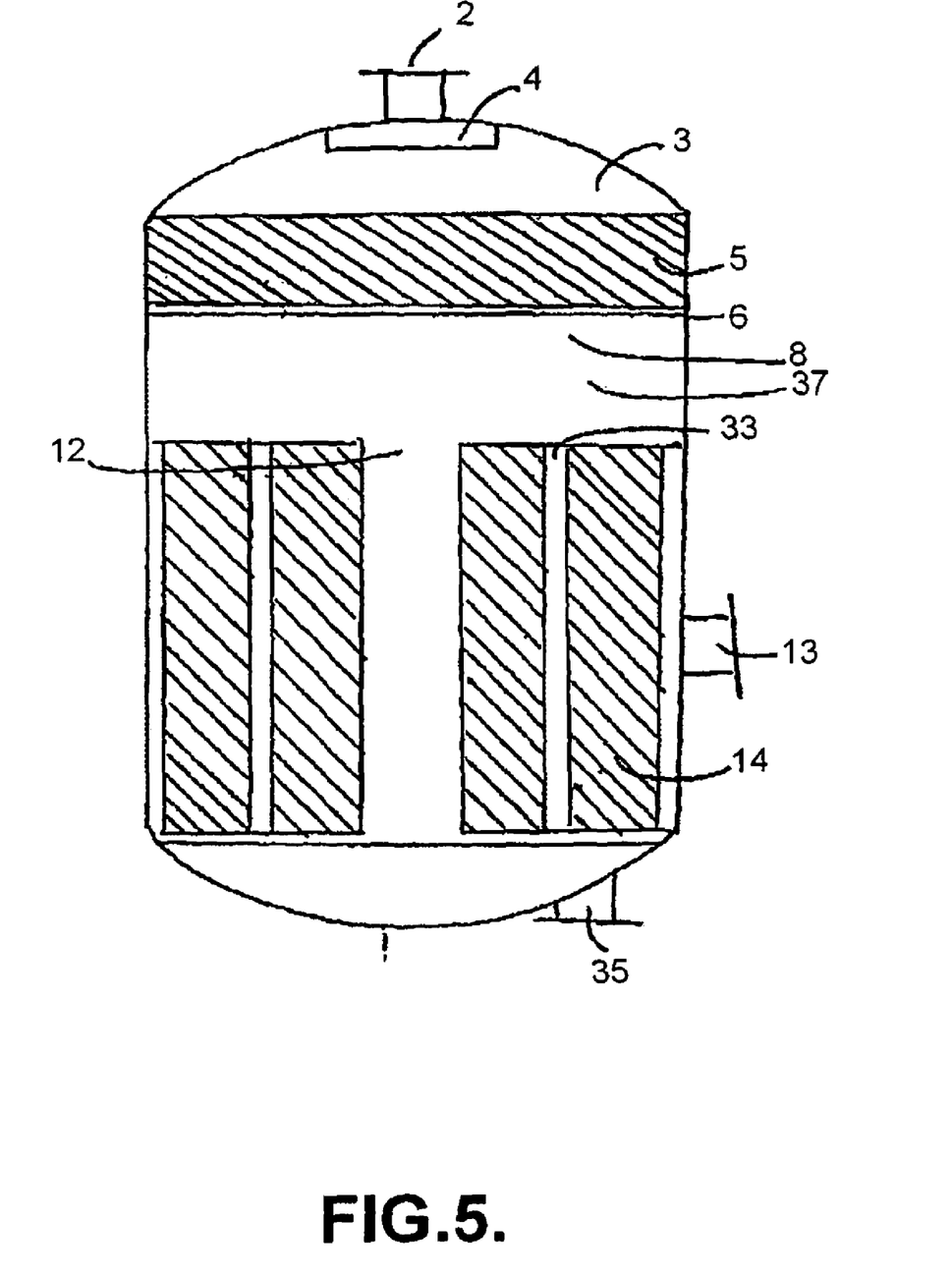
FIG. 5 is a schematic diagram of a reactor system according to the subject invention.

This performance data is for new catalyst which has been un-aged by plant operation. The distribution of catalyst volume verses temperature within the reactors is illustrated in FIG. 4. As can be seen, from the arrangement of the present invention of Example 1 has 49% of the catalyst operating above a temperature of 250° C. In contrast, in the single volume arrangement of Comparative Example 1 and FIG. 3, the total amount of catalyst is increased to 110% of that of Example 1 and 60% of this catalyst is operating above 250° C.

Thus it would be understood that the arrangement of the present invention allows the amount the catalyst required to be reduced, for an improved performance with the same amount of the catalyst, and for the catalyst to be operated at lower temperatures which will prolong catalyst life.

Whilst the present invention has been discussed with regard to the production of methanol from synthesis gas, it will be understood that the reactor design of the present invention may also be applied to other exothermic chemical reactions, such as the formation of ammonia.

The invention claimed is:

1. A reactor system for use in the production of methanol from synthesis gas comprising:
  (a) a first reactor adapted to be maintained under methanol synthesis conditions having an inlet for supply of synthesis gas and an outlet for recovery of a first methanol-containing stream, said first reactor being charged with a first volume of a methanol synthesis catalyst through which the synthesis gas flows and on which in use, partial conversion of the synthesis gas to a product gas mixture comprising methanol and un-reacted synthesis gas will occur, said first reactor not including cooling means such that said first reactor provides such conversion adiabatically; and
  (b) a second reactor adapted to be maintained under methanol synthesis conditions having an inlet for supply of the gaseous first methanol-containing stream which has not been subjected to cooling after being recovered from the outlet of the first reactor, an outlet for recovery of a second methanol-containing stream and indirect cooling means, said second reactor being charged with a second volume of a methanol synthesis catalyst through which the gaseous first methanol-containing stream flows radially from the inlet and on which, in use, further conversion of the synthesis gas to a product gas mixture comprising methanol will occur,
  wherein said first and second reactors are located in separate reactors or, said first and second reactors are zones located within a single reactor, with the first catalyst and the second catalyst being separated from each other; and
  wherein the reactor system does not include cooling means located between the outlet of the first reactor and the inlet of the second reactor.

2. A reactor system according to claim 1 wherein the first and second reactors are located in separate reactors and the outlet of the first reactor is connected to the inlet of the second reactor.

3. A reactor system according to claim 1 wherein the first and second reactors are located within a single reactor.

4. The reactor system according to claim 1 wherein the catalyst volume of the first reactor is arranged with a substantially horizontal orientation.

5. The reactor system according to claim 1 wherein the depth of the first catalyst volume is less than its horizontal dimensions.

6. The reactor system according to claim 1 wherein the first reactor additionally includes an inlet gas distributor.

7. The reactor system according to claim 1 wherein the second volume of catalyst is arranged such that the inlet is located centrally and the outlet is located at a reactor wall, such that the product stream from the first reactor flows radially from the inlet through the second catalyst volume to the outlet.

8. The reactor system according to claim 1 wherein the cooling of the catalyst in the second reactor is provided by water cooling in tubes which pass through the catalyst bed.

9. The reactor system according to claim 8 additionally including apparatus to enable steam produced by the water cooling to be used to drive a compressor.

10. A plant for the production of methanol from a synthesis gas mixture comprising carbon oxides, hydrogen and methane comprising:
(a) a methanol synthesis zone including the reactor system according to claim 1; and
(b) a methanol recovery zone, adapted to be maintained under methanol recovery conditions, for recovery of a crude methanol product stream from the product gas mixture, and for recovery of a vaporous stream comprising un-reacted material of the synthesis gas.

11. The plant according to claim 10 additionally including:
(c) means for recycling at least a portion of the un-reacted material of the synthesis gas to the methanol synthesis zone.

12. The plant according to claim 10 comprising a plurality of reactor systems according to claim 1.

13. The plant according to claim 12 wherein the plurality of reactor systems are located in parallel or in series.

14. The plant according to claim 10, wherein the synthesis gas mixture is produced from a hydrocarbon feedstock material in plant comprising a steam reforming zone, adapted to be maintained under steam reforming conditions and charged with a catalyst effective for catalysis of at least one steam reforming reaction, for steam reforming of a vaporous mixture of the hydrocarbon feedstock in the steam to form a synthesis gas mixture comprising carbon oxides, hydrogen and methane.

15. The plant according to claim 11, wherein the synthesis gas mixture is produced from a hydrocarbon feedstock material in plant comprising a steam reforming zone, adapted to be maintained under steam reforming conditions and charged with a catalyst effective for catalysis of at least one steam reforming reaction, for steam reforming of a vaporous mixture of the hydrocarbon feedstock in the steam to form a synthesis gas mixture comprising carbon oxides, hydrogen and methane.

16. The plant according to claim 12, wherein the synthesis gas mixture is produced from a hydrocarbon feedstock material in plant comprising a steam reforming zone, adapted to be maintained under steam reforming conditions and charged with a catalyst effective for catalysis of at least one steam reforming reaction, for steam reforming of a vaporous mixture of the hydrocarbon feedstock in the steam to form a synthesis gas mixture comprising carbon oxides, hydrogen and methane.

17. The plant according to claim 13, wherein the synthesis gas mixture is produced from a hydrocarbon feedstock material in plant comprising a steam reforming zone, adapted to be maintained under steam reforming conditions and charged with a catalyst effective for catalysis of at least one steam reforming reaction, for steam reforming of a vaporous mixture of the hydrocarbon feedstock in the steam to form a synthesis gas mixture comprising carbon oxides, hydrogen and methane.

* * * * *